ized Patent

United States Patent [19]
Shioya et al.

[11] Patent Number: 4,997,425
[45] Date of Patent: Mar. 5, 1991

[54] WOUND DRESSING

[75] Inventors: Nobuyuki Shioya, Yokohama; Yoshimitsu Kuroyanagi, Hachioji; Yasumi Koganei, Atsugi; Ryuichiro Yoda, Yokohama, all of Japan

[73] Assignee: Nippon Zeon Co., Ltd., Tokyo, Japan

[21] Appl. No.: 501,980

[22] Filed: Mar. 29, 1990

Related U.S. Application Data

[63] Continuation of Ser. No. 346,330, May 1, 1989, abandoned, which is a continuation of Ser. No. 110,907, Oct. 21, 1987, abandoned.

[30] Foreign Application Priority Data

Oct. 31, 1986 [JP] Japan ............................ 61-260002
Oct. 31, 1986 [JP] Japan ............................ 61-260003
Oct. 31, 1986 [JP] Japan ............................ 61-260142

[51] Int. Cl.$^5$ .................. A61F 13/00; A61L 15/00
[52] U.S. Cl. .................. 604/304; 604/369; 604/378; 128/156
[58] Field of Search .......... 604/304, 369, 378, 384; 623/15; 128/156, DIG. 8

[56] References Cited

U.S. PATENT DOCUMENTS

| | | | |
|---|---|---|---|
| 2,140,026 | 9/1935 | Murphy et al. | 128/156 |
| 2,533,004 | 12/1950 | Ferry et al. | 128/156 |
| 2,610,625 | 9/1952 | Sifferd et al. | 604/369 |
| 3,113,568 | 12/1963 | Robins | 604/369 |
| 3,648,692 | 3/1972 | Wheeler | 604/369 |
| 3,800,792 | 4/1974 | McKnight et al. | 128/156 |
| 3,867,520 | 2/1975 | Mori et al. | 604/304 |
| 3,949,742 | 4/1976 | Nowakowski | 128/156 |
| 4,060,081 | 11/1977 | Yannas et al. | 128/DIG. 8 |
| 4,161,948 | 7/1979 | Bichon | 128/156 |
| 4,360,015 | 11/1982 | Mayer | 128/156 |
| 4,606,337 | 8/1986 | Zimmermann et al. | 604/369 |
| 4,642,118 | 2/1987 | Kuroyanagi et al. | 623/15 |
| 4,784,653 | 11/1988 | Bolton et al. | 604/307 |

OTHER PUBLICATIONS

Adams et al., "The Sulfadiazine Treatment of Burns," The Southern Surgeon, May 1942, pp. 324–340.
Oluwasanmi et al., "A Comparative Study of Four Materials in Local Burn Care in Rabbit Model", The Journal of Trama, vol. 16, No. 5, pp. 348–353, May 1976.

*Primary Examiner*—C. Fred Rosenbaum
*Assistant Examiner*—Sharon Rose
*Attorney, Agent, or Firm*—Armstrong, Nikaido, Marmelstein, Kubovcik & Murray

[57] ABSTRACT

A wound dressing having a porous layer with a good affinity to tissue of organisms comprising (a) a first layer to be placed on the wound surface having pores of 20 to 500 μm in diameter, and 1 to 10 mm thick, and (b) a second layer remote from the wound surface having pores not more than 20 μm in diameter, and 0.5 to 5 μm thick. The first layer can be provided with an antimicrobial of not more than 50% by weight, and the second layer can contain an antimicrobial of 10 to 80% by weight.

12 Claims, 2 Drawing Sheets

WOUND DRESSING

BACKGROUND OF THE INVENTION

This application is a continuation of application Ser. No. 346,330, abandoned, which is a continuation-in-part of No. 110,907, now abandoned.

1. Field of the Invention

The present invention relates to a wound dressing, and more particularly to a wound dressing for use in treating wounds, such as burns and those due to trauma.

2. Description of the Prior Art

So far, there has been developed a variety of dressings for use in treating skin defects extending over a wide area resulting from a burn or trauma, and these are roughly grouped into three types:

(1) Grafts, such as a homogenous or heterogenous thick-split graft of human amnion;

(2) Reconstruction materials from bodily substances, such as collagen membrane (non-woven fabric) and fibrin membrane; and (3) Synthetic high molecular materials, typically with a dual-layer structure of silicon film and nylon knitting.

All of the three dressings, however, have difficulties. Grafts are advantageous and useful for controlling insensible perspiration and for preventing the transudation of body liquids while, from an immunological standpoint, have a disadvantageous strong rejection to tissue only providing a short duration of dressing effect. Reconstruction materials, in particular, collagen material owing to a stable supply, is mostly used. However, its antigenicity can be weakened by enzyme treatment and is rapidly decomposed and absorbed into the body, and is thus useless for a long lasting dressing. The synthetic high molecular materials are absorbed in the body without being subjected to decomposition and thus have low antigenicity. A stable supply of this material is possible and sterilizable. On the other hand, generally this material presents a problem of having an inadequate affinity to tissue.

Also, there exist materials of woven or sponge structure with silicon film adhered to one surface so as to prevent bacteria from invading, and exhibit the favorable properties of absorbing exudate from affected areas. Further, fibrin is produced therein (the so-called primary vital adhesion), and subsequent spreading of fibroblasts and capillaries provides firm adhesion of the dressing to the wound (the so-called secondary vital adhesion). The difficulty however encountered in the use of this material is the tendency, observed under the silicon film, towards aggregation of body fluid proteins accompanied by a high danger of permitting bacteria already present on the wound surface to utilize the body fluid as nourishment for their propagation, resulting in hindering of the healing of the wound.

A countermeasure against such infection is at present made by applying cream or ointment containing local antimicrobial to the surface of the wound, and has been revealed in the application of different wound dressings to be not very useful for preventing growth of the foreign bacteria.

OBJECTS AND SUMMARY OF THE INVENTION

An object of the present invention is to remove the above-mentioned defects or shortcomings involved in the prior art materials, and to provide a wound dressing useful for absorbing exudate from a wound to prevent the exudate remaining between the dressing material and the surface of the wound; permitting tissues to develop; and capable of protecting against the invasion of foreign bacteria with the result of promoting therapeutic effects.

Another object of the present invention is to provide a wound dressing capable of preventing bacterial infection of the wound and transudation of body fluids, and thus enabling fast healing of the wound.

A further object of the present invention is to provide a wound dressing of a multilayer structure and containing a therapeutic agent so that the above-mentioned therapeutic effects can be displayed satisfactorily.

The first embodiment of the invention is a wound dressing having a porous layer with a good affinity to tissue of an organism, said dressing comprising (a) a first portion to be placed in contact with the wound surface having pores of 20 to 500 μm diameter, and being 1 to 10 mm thick, and (b) a second portion positioned remote from the wound surface having pores of not more than 20 μm in diameter, and being 0.5 to 5 μm thick.

The first embodiment of the wound dressing preferably comprises a sponge layer and an outer surface layer overlaying the sponge layer, the layers being made from a polyamino acid superior in affinity to tissues of organisms, the sponge layer having pores of 20 to 500 μm in diameter and being 1 to 10 mm thick, and the outer surface layer having pores of not more than 20 μm in diameter and being 0.5 to 5 μm thick.

Suitable polyamino acids for use in the invention are poly-α-amino acids having good affinity to tissues of organisms and soluble in solvents permitting freeze-drying, and typical examples are poly(L-leucine), poly(-benzyl-L-glutamate), copoly(L-lysine-L-leucine), copoly(L-lysine-L-glutamic acid), etc. The wound dressing may preferably be composed of a sponge having an outer surface (crust) layer of such a polyamino acid.

The wound dressing is applied to the wound with the sponge layer having pores of 20 to 500 μm in diameter and 1 to 10 mm thick in contact with the surface of the wound. The pores in the sponge layer preferably extend from the wound surface to the interface of both layers and have decreasing diameters in the same direction. Pore diameters below 20 μm may result in the poor development of tissue and insufficient absorption of exudate while pore diameters above 500 μm may produce inadequate adhesiveness to the wound surface allowing exudate to remain. Thus, pore diameters outside the range are unsuitable for treatment of wounds. Thicknesses of the sponge layer below 1 mm may result in poor development of tissue and insufficient absorption of exudate, and those above 10 mm may produce inconvenient handling. Thus, thicknesses outside the range are unsuitable.

The outer surface layer having pores up to 20 μm in diameter, and 0.5 to 5 μm thick is positioned remote from the wound surface when the wound dressing is applied to the wound, and plays the role of preventing foreign bacteria from invading into the wound. If the pore diameter is 20 μm or more, or the thickness is less than 0.5 μm, the usefulness may be unsatisfactory. Thicknesses of 5 μm or more may result in inadequate permeability to vapor and oxygen, accompanied by undesired effects.

The wound dressing is made, for example, by the following procedure. A poly-α-amino acid solution is poured into a specified vessel and converted into gel at room temperature. After the surface is dried with warm air, the gel is cooled suddenly to a frozen state, and dried under vacuum. A wound dressing consisting of a crust layer or outer surface layer, and a sponge layer formed in the vessel is obtained.

The thus-obtained wound dressing is useful for absorbing exudate and for the production of fibrin resulting in primary vital adhesion. Subsequently, owing to primary vital adhesion with the spread of fibroblasts and capillaries, secondary vital adhesion occurs, thus contributing to fast healing of the wound. Thus, a wound dressing for treating wounds, such as those resulting from burn or trauma, in particular having a sufficient adherence to the wound and not allowing exudate to remain between the dressing material and the surface of wound with the effects of promoting healing of the wound, can be provided.

As understood from the above-stated, the first embodiment of the wound dressing according to the invention comprises a sponge layer of specified pore diameter and specified thickness. The wound dressing is useful for effectively absorbing exudate to produce a firm primary vital adhesion to the surface of wound, and which is useful under these conditions, for vigorous development of fibroblast and capillaries. with the good effect of secondary vital adhesion The outer surface layer of specified pore diameter and specified thickness plays the role of controlling insensible perspiration owing to its permeability to water vapor and preventing foreign bacteria from invading, thus contributing effectively to fast healing of a wound.

The second embodiment of the invention is a wound dressing having a porous layer having a good affinity to tissues of organisms comprising (a) a first portion to be placed on the wound surface and having pores of 20 to 500 $\mu$m in diameter, 1 to 10 mm thick, and containing an antimicrobial in not more than 50% by weight, and b) a second portion located remote from the wound of not more than 20 $\mu$m in pore diameter 0.5 to 5 $\mu$m thick, and containing an antimicrobial in an amount of 10 to 80% by weight.

The second embodiment of the wound dressing contains in the porous layer an antimicrobial capable of destroying bacteria present on the wound and preventing infection due to invading foreign bacteria. For achieving this, the antimicrobial is desired to be released constantly very little by very little. Generally speaking, medicine contained in a hydrophilic high molecular weight material is readily released when the material is saturated, and therefore long time release of medicine is unexpected when the medicine is contained in such a hydrophobic high molecular weight material. If the latter is a film, it readily releases medicine from the crystalline region of the film through the influence of diffusion allowing medicine stored inside of the film to be readily released. Thus, it is difficult to control the release rate when using a hydrophobic high molecular weight material. For solving this difficulty, according to the invention, the base material of the porous layer is made especially from hydrophobic poly-$\alpha$-amino acid with the effect of remarkably limiting circulation or diffusion of liquid in the layer and as the result, enabling long time release of medicine. It has been demonstrated that for example, sulfadiazine silver used as a medicine was released at an approximately constant rate from the wound dressing according to the invention in physiological saline solution over the period of about one month.

The second embodiment of the wound dressing according to the invention has a unique construction of the porous layer. To attain the above-mentioned effects, the wound dressing comprises a first portion to be placed on the wound surface, and a second portion located remote from the wound surface with the portions having specified ranges of pore diameter, thickness and content of antimicrobial.

As to the first portion, which plays a very important part for the absorption of exudate (body fluids) from the wound and the development of tissue, pore diameters less than 20 $\mu$m (or too small) may result in poor development of tissue and insufficient absorption of exudate while pore diameters of 500 $\mu$m or more (or too great) may produce inadequate adhesiveness to the wound surface to allow exudate to remain. Accordingly, the range of pore diameters should be 20 to 500 $\mu$m, preferably 50 to 200 $\mu$m. In addition, the thickness of the first portion should be 1 to 10 mm, preferably 2 to 5 mm, because a thickness of less than 1 mm is too thin to allow full development of tissues and thorough absorption of exudate, and those exceeding 10 mm may result in inconvenience or disadvantages in handling and moldability.

Regarding the second or the outermost portion, which is useful for preventing foreign bacteria from invading, pore diameters exceeding 20 $\mu$m allow bacteria to pass through them into the tissue. The pore diameter is desirably about 1 $\mu$m as the lower limit for allowing oxygen and water vapor to pass and for controlling insensible perspiration. The thickness should be not less than 0.5 $\mu$m for preventing bacteria from invading, and on the other hand, too great of a thickness is unsuitable, and should be not more than 5 $\mu$m for the same reason as above-stated for the first embodiment. In particular, the second portion is desirably 1 to 3 $\mu$m in thickness.

In the first portion or porous layer, it is desirable to have pores extending from the surface, to be placed on the wound surface, towards the second or outer surface portion, and to have these pores decreasing in diameter in the same direction. The outer surface layer (the second portion) desirably has a uniform film structure. This construction enables thorough absorption of exudate from the wound and good development of tissue, and strictly prevents foreign bacteria from invading.

The second embodiment of the wound dressing according to the invention contains antimicrobial in the porous layer so that the antimicrobial may be released little by little. For realizing this, the first portion should contain antimicrobial in 0 to 100 parts to 100 parts of polymer base substance or 0-50% by weight. The content should be 50% or less by weight because otherwise inadequate pliability of the dressing material results. It is preferably 30 to 50% by weight. The second portion should contain antimicrobial in 10 to 80% by weight because contents of not more than 10% by weight are associated with undesirable short duration of antimicrobial release while contents exceeding 80% by weight result in insufficient pliability. The contents of antimicrobial in the second portion is preferably 30 to 50% by weight.

Suitable poly-$\alpha$-amino acids superior in affinity to tissues for use in the second embodiment of the present invention are poly( -benzyl-L-glutamate)(PBLG), poly(L-leucine), poly(N-carbobenzoxy-L-lysine), and combinations of these. These, which are hydrophobic, readily polymerize and are soluble in benzene or dioxane allowing freeze-drying under vacuum, are of good workability, and thus suitable to be molded.

Examples of local antimicrobial agents suitable for use in the second embodiment of the wound dressing according to the invention are sulfadiazine silver, sulfadiazine zinc, sulfadiazine cerium, silver nitrate, gentamicin, etc. The wound dressing according to the second invention is made from a mixture of a substance to be molded and an antimicrobial added thereto.

The second embodiment of wound dressing according to the invention may be made in the process comprising adding a predetermined amount of antimicrobial to a solution of substance to be molded, such as poly-α-amino acid, pouring the resulting solution into a vessel or mold, and then subjecting to quenching and freeze-drying under vacuum so that a sheet-molded porous layer is produced.

In combination with the antimicrobial, other medicines such as a vasoconstrictor for hemostasis and an analgesic may be contained in the porous layer.

The first and second embodiments of the wound dressing according to the present invention may be preferably coated on at least one surface with a substance having a high affinity to tissues for accelerating wound healing, especially the surface to be placed on the wound surface This contributes to promotion of initial vital adhesion, prevention against exudate remaining between the wound surface and the facing surface of the dressing, and in turn fast healing of the wound Instead of the coating, a similar substance-containing layer overlaying the porous layer may be formed. The coating or formation of the overlaying layer is followed by freeze-drying. As suitable substances for this purpose are enumerated serum proteins, such as fibrinogen, albumin, globulin, fibronectin, etc., collagen including atherocollagen, gelatin, mucopolysaccarides, etc. Alternately, the wound dressing may be impregnated with the substance having a high tissue affinity.

Fibrinogen is a blood clotting factor which is converted by the action of thrombin into fibrin. Fibrin has a very good adhesiveness to fibroblasts and supports their growth. Coating of it to the surface of the dressing to be placed on the wound surface therefore produces the effects of hemostasis and full vital adhesion, in turn contributing to healing. Like fibrin, collagen has a high adhesiveness to fibroblasts and can promote their growth, thus producing similar effects.

The first and second embodiments of the wound dressing according to the present invention may preferably be modified to have a reinforcing material embedded in the porous layer. The modified wound dressing is obtained in a process comprising pouring a solution such as poly-α-amino acid to be molded, if desired containing a predetermined amount of antimicrobial added thereto, into a mold including a reinforcing material such as silicone gauze or nylon mesh therein, and then subjecting the mold to quenching and freeze-drying under vacuum to mold a sheet of a porous layer.

The reinforcing material embedded in the porous layer endows mechanical strength to the wound dressing having the porous layer, and in addition plays an important part in facilitating peeling off of the porous layer, for example, after treatment with the wound dressing for second and third degree burns over a certain period. With this embodiment, the base substance may remain in the tissue, but it can be decomposed and absorbed into the body. As understood from this, the first portion of the porous layer must have an appreciable thickness (1 to 10 mm) as previously defined, otherwise the part closely adhered to the tissue will also be removed from it.

It is desirable that the wound dressing is moderately flexible to allow displacement of the concerned body part or site. Poor flexibility can cause accidental peeling off of the wound dressing. To endow such flexibility as stated, it is desirable that the reinforcing material is elastic. For use in the present invention as suitable reinforcing materials, natural fibers such as protein, cellulose and mineral, and others; synthetic fibers such as polyurethane, polyolefin, polyvinyl chloride, polyvinylidene chloride, polyamide, silicone, polyester, and others; metallic fibers such as stainless steel, copper, and others are acceptable. These are useful particularly in the form of mesh, such as nylon mesh and silicone gauze.

Other objects, features and advantages of the invention will appear more fully from the following detailed description thereof taken in connection with the accompanying drawings.

BRIEF DESCRIPTION OF THE DRAWINGS

The drawings show illustrative embodiments of the present invention.

DESCRIPTION OF THE PREFERRED EMBODIMENTS

Embodiments of the present invention will be described in detail with reference to the accompanying drawings hereinafter.

Figure 1:
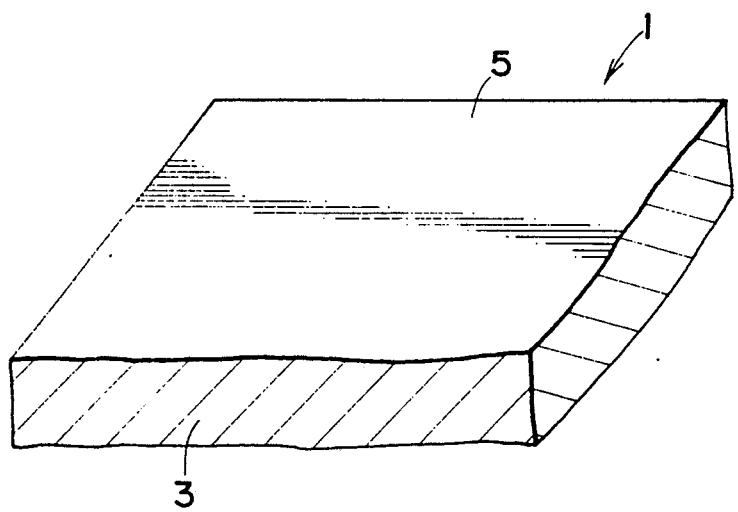
FIG. 1 is a fragmentary perspective view of a wound dressing according to the invention.
Figure 2:
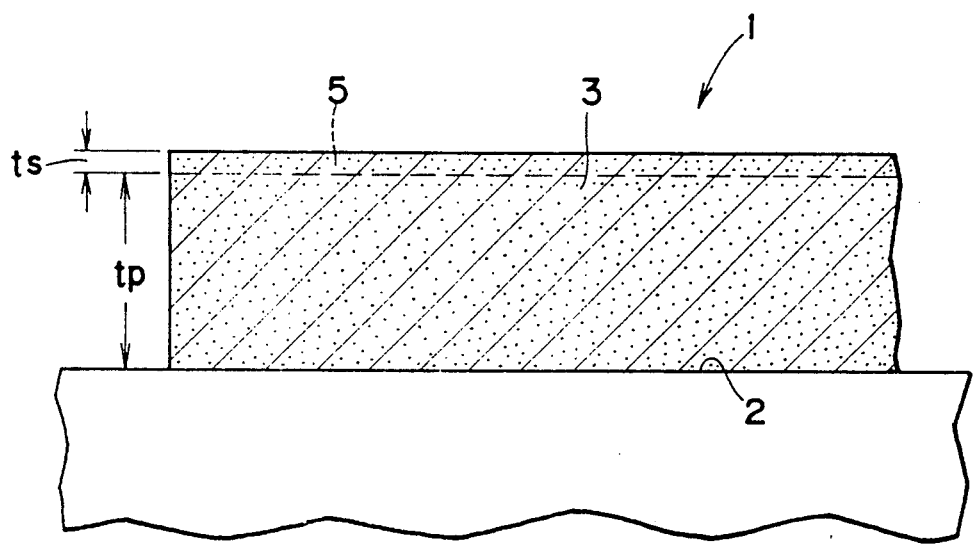
FIG. 2 is a cross-sectional view of the same drawn to an enlarged scale.

FIG. 1 illustrates a fragmentary perspective view of a wound dressing 1 according to the present invention, and FIG. 2 is a cross-sectional view of the same. The dressing 1 consists of a porous layer 3 to be closely adhered to the surface of a wound 2 and an outer surface layer 5 of uniform structure having pores of extremely small diameter overlaying the porous layer 3.

The porous layer 3, corresponding to the above-mentioned first portion, is made from poly-L-leucine and has an overall thickness, $t_p$ of 1 to 10 mm, for example, about 2 mm. The pores in the porous layer 3 are from 20 to 500 $\mu$m in diameter, preferably 50 to 200 $\mu$m in diameter and formed so as to have a decreasing diameter in a direction from the surface, to be placed on the wound surface, towards the outer surface layer 5. The porous layer 3 may be provided with local antimicrobial, such as sulfadiazine silver at 50% by weight or less, as in a second embodiment of the present invention.

Figure 4:
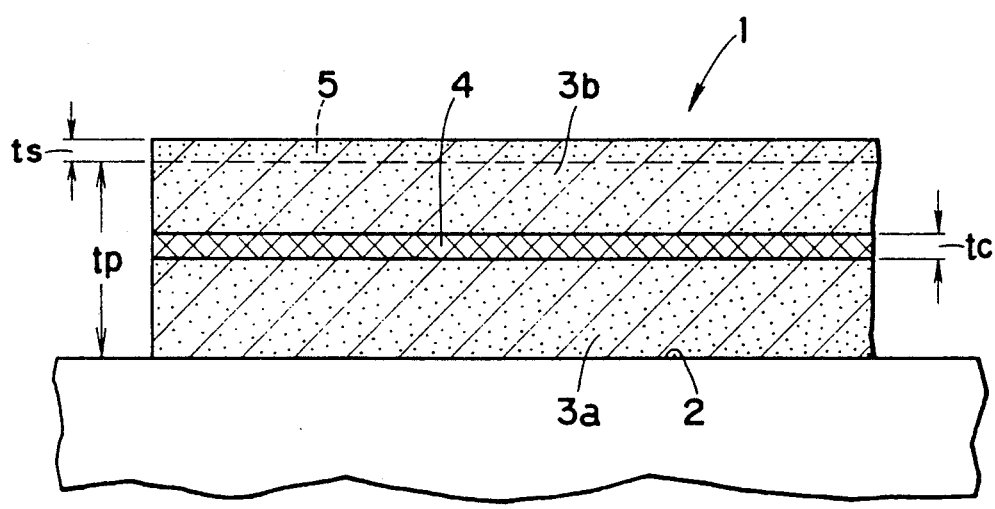
FIG. 4 is a cross-sectional view of the embodiment of FIG. 3 drawn to an enlarged scale.

Likewise, the outer surface layer 5, which corresponds to the above-stated second portion, is made from poly-L-leucine and defined by the dashed line, in FIGS. 2 and 4, and has a thickness, $t_s$ of 0.5 to 5 $\mu$m, preferably 1 to 3 $\mu$m. The pores in outer surface layer 5 are formed so as to be very small and up to 20 $\mu$m, such as several $\mu$m, in diameter. The outer surface layer 5 may contain, as in the second embodiment of the invention, a local antimicrobial, such as sulfadiazine silver at 10 to 80% by weight, preferably 30 to 50% by weight.

Figure 3:
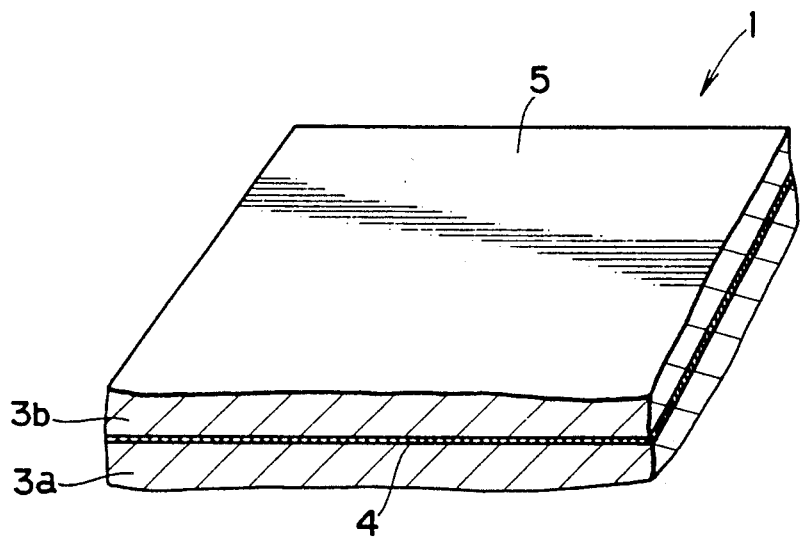
FIG. 3 is a fragmentary perspective view of an alternative embodiment of the present invention.

FIG. 3 illustrates, in a fragmentary perspective view, another embodiment of the wound dressing 1 according to the invention, and FIG. 4 is a cross-sectional view of the same. This dressing 1 consists of a lower porous layer 3a to be closely adhered to the surface of wound 2, an upper porous layer 3b, a reinforcing intermediate material layer 4, such as nylon mesh, and an outer surface layer 5 of uniform structure having pores of very small diameter overlaying the upper porous layer 3b.

The porous layers 3a, 3b, each constituting the aforementioned first portion, are made from poly-L-leucine and have a total thickness, $t_p$, including the intermediate material layer 4, of 1 to 10 mm, for example, about 2 mm. The thickness of the intermediate material layer 4 is expressed as $t_c$. The pores in the porous layers 3a, 3b are from 20 to 500 μm, preferably 50 to 200 μm, in diameter, and are formed so as to have a decreasing diameter in the direction from the wound surface towards the outer surface layer 5. The porous layers 3a, 3b may contain local antimicrobial, such as sulfadiazine silver at 50% by weight or less, as in the second embodiment of the invention.

The embedded mesh-shaped intermediate material layer 4 for reinforcing the porous layers 3a, 3b may desirably have a thickness, $t_c$ of from 10 to 100 μm, and a mesh size from 1 to 2 mm. The polymer forming the porous layers 3a, 3b penetrates the mesh of the intermediate material layer 4.

The outer surface layer 5 is the same as that of FIG. 2. The reinforcing intermediate material layer 4 may be embedded, for example, at about the middle level in relation to the overall thickness of the dressing, for instance, 1 mm deep when the overall thickness is 2 mm. Otherwise, for example, the intermediate material layer 4 may be embedded nearer to the outer surface layer 5 or the lower surface to be placed in contact with the wound surface, though the location is desirable at depths of about 0.5 mm or more from either surface but not necessarily that deep.

In the following Examples, the invention will be described.

EXAMPLE 1

N-carboxyl anhydride of L-leucine was dissolved in benzene and polymerized with triethylamine as an initiator. The poly(L-leucine) was dissolved in benzene to a concentration of 0.5 g/dl, and this poly(L-leucine) solution (30 ml) after being warmed to 70° C. (because it is a gel at room temperature), was poured into an aluminum vessel (10 cm×15 cm). After it gelled at room temperature, only the surface of the gel was dried with warm air at a temperature about 50° C. Then, the benzene was evaporated to make the concentration of polymer in the gel higher, and in turn cooling to −30° C. to a frozen state, and freeze-drying under vacuum to obtain a wound dressing according to the invention were conducted. This product was of a multilayer structure consisting of a uniform (i.e., substantially unmeasurable pore diameter) crust layer of about 1.4 μm thick, and a sponge layer of about 2.4 mm thick and having pores of decreasing diameter of from 300 to 400 μm at the surface to be adhered to the wound surface to 50 to 100 μm at the surface interfacing the crust layer.

This wound dressing was evaluated with 6–8 week old rats. Each rat was subjected to surgery in the dorsal region on one side to create a full thickness skin defect (3 cm×2.5 cm). The wound dressing was applied to the rat and sutured. Then, gentamicin ointment was applied to the circumference, a Telfa pad was sutured and elastic bandage was applied.

At 4 weeks after the application of such a dressing, the dressing was removed together with the surrounding tissue, stained with hematoxylin-eosin, and examined histologically with the results of good vital adhesion, and the development of tissue into the sponge, poor appearance of foreign body giant cell, and, in the lower zone of the sponge layer, the new tissue was abundant in capillaries. The dressing was peeled off with minor bleeding, and the tissue surface observed had a good appearance and was in somewhat of a dry state suggesting control of insensible perspiration.

EXAMPLE 2

An aqueous solution of copoly(L-Leucine-L-lysine)(30 ml) was poured into an aluminum vessel (10 cm×15 cm), and the surface was dried with warm air at a temperature of about 50° C., followed by freeze-drying under vacuum in the same manner as in Example 1. Subsequently, a 24 hour treatment at 25° C. with 10% hexamethylene diisocynate in acetone was carried out while intermolecular crosslinking reaction was effected, well washed with acetone. The resulting insoluble sponge was sterilized with ethylene oxide gas. Thus, an alternative wound dressing according to the invention was obtained.

This wound dressing comprised sponge and crust layers, the sponge layer having a thickness of about 2 mm with pores having decreasing diameter from about 300 to 400 μm at the surface to be brought into contact with the wound surface to 50 to 100 μm at the boundary with the crust layer, in the same manner as in Example 1, and the crust layer having a thickness of about 1.0 μm.

This wound dressing or sponge (portion 1 cm², thickness 3 mm) obtained by intermolecular cross-linking was applied subcutaneously in the dorsal region of a 5-week old rat. At 4 weeks, evaluation was made by observation of the reaction with the body, in the same process as in Example 1, a preparation was made, stained and the cross-sectional view was examined There was observed fibroblasts and capillaries in the lower portion of the sponge with no capsules of connective tissue at the edges of the sponge.

EXAMPLE 3

A dioxane solution of poly( -benzyl-L-glutamate)(30 ml) was poured into an aluminum vessel (10 cm×15 cm), and reacted in the same manner as in Example 1 to obtain another embodiment of the wound dressing according to the invention. This wound dressing comprised a sponge layer of about 3 mm thick with pores of decreasing diameter from about 300 to 450 μm at the surface to be placed in contact with wound surface to 50 to 100 μm at the boundary with the crust layer, and a crust layer of about 1.5 μm in thickness.

This wound dressing was evaluated in the same way as in Example 1.

This wound dressing was applied to the full-thickness skin defect in the dorsal region of a rat, and at 10 days, an examination with a scanning electron microscope was carried out to determine the adhesion of the wound dressing to the tissue from a structural viewpoint and the opened surface of it. There was observed development of tissue in the sponge, and fibrin structure on the opened surface.

COMPARISON 1

In the same way as in Example 1, a wound dressing was obtained with a solution of poly(L-leucine) in benzene, excluding drying of the surface with warm air at a temperature of 50° C. The dressing had no crust but only a single layer of sponge. The thickness was 2.5 mm with pores, at the surface to be adhered to wound surface, having a diameter of 300 to 400 μm.

COMPARISON 2

The same solution as used in Example of poly(L-leucine) in benzene, was poured into an aluminum vessel, changed into gel at room temperature, and then the whole was dried with warm air at a temperature of about 50° C. In turn, quenching to a frozen state of −30° C., and freeze-drying under vacuum followed. The thus-obtained wound dressing comprised a single layer of the same phase as the above-mentioned crust layer, and the thickness was 1 mm.

The wound dressings obtained in Comparisons 1 and 2 were evaluated in rats in the same way as in Example 1. The product of Comparison 1 showed the surface remaining inflamed and having poor development of new tissues, this being probably due to the invasion of foreign bacteria.

Examination of the wound dressing of Comparison 2 revealed remaining exudate, and neither vital adhesion nor development of new tissue. This is considered to be due to the absence of a type of sponge layer allowing development of tissues thereinto, resulting in poor vital adhesion, and in turn exhibiting insufficient absorption of body liquid with exudate remaining on the wound surface.

EXAMPLE 4

A mixture of poly(L-leucine) with sulfadiazine silver was dissolved in benzene to make a concentration of 0.25 g/dl, and poured into an aluminum vessel. The polymer solution was, after only the surface was dried with warm air, quenched at −30° C., and subjected to freeze-drying under vacuum to obtain a sheet-molded wound dressing.

This wound dressing could be gas-sterilized and kept in darkness. Alternately, it was coated with a substance having good affinity to tissue or promoting healing of the wound in the procedure, it was immersed in ethanol, and washed with sterilized distilled water. On the porous layer 3 of the wetted wound dressing, an aqueous solution of human fibrinogen (concentration 1 g/dl) was coated. Subsequently, quenching to −20° C., freeze-drying, and ultraviolet ray radiation in a sterile room for several hours were in turn carried out, and the product was kept at 5° C. in darkness.

This wound dressing was evaluated in 6-8 week old rats with each rat being subjected to surgery in the dorsal region on one side to create a full thickness skin defect (3 cm × 2.5 cm). The wound dressing was applied and sutured to it, gentamicin ointment was applied to the circumference, a Telfa pad was sutured on, and an elastic bandage was applied thereto. The application of the wound dressing was made by merely lightly pressing it on the wound for over about 1 minute with the result of moderate adhesion so that suturing of the wound dressing was carried out without allowing it to move. This may be probably owed to the adhesive action of fibrin converted from the fibrinogen in the lower portion of the layer. The wound dressing demonstrated good hemostatic effect on minor bleeding such as oozing on the wound surface. The adhesive and hemostatic effects initially may more likely contribute to prevention against ecchymoma underneath the dressing. At 2 and 4 weeks, histological findings showed good vital adhesion, and development of new tissue abundant in capillaries in the lower portion of the layer.

EXAMPLE 5

A mixture of poly(L-leucine) with sulfadiazine silver was dissolved in benzene to make a concentration of 0.25 g/dl, and poured into an aluminum vessel having a nylon mesh previously set at a level of 1 mm from the bottom. The polymer solution was, after only the surface was dried with warm air, quenched at −30° C., and subjected to freeze-drying under vacuum to obtain a sheet-molded wound dressing.

This wound dressing was gas-sterilized, and coated with a substance having good affinity to tissue or the like in the same way as in Example 4. Evaluation of this wound dressing was made in 6-8 week old rats with similar good results. Each rat was subjected to surgery in the dorsal region to create a full thickness skin defect. Then the wound dressing was applied to it merely by light pressing over the wound for about 1 minute, with the result of moderate adhesion preventing it from movement. It demonstrated a good hemostatic effect on minor bleeding such as oozing of the wound surface. At 2 and 4 weeks, histological findings showed good vital adhesion, and development of new tissue abundant in capillaries in the lower portion of the layer.

It will be evident that various modifications can be made to the described embodiments without departing from the scope of the present invention.

What is claimed is:

1. A wound dressing of a porous layer structure having good affinity to tissues of organisms comprising:
   (a) a first portion having a reinforcing material embedded therein, said first portion adapted to be placed on the wound surface and having a thickness of 1 to 10 mm;
   (b) a second portion superimposed on the first portion, said second portion having a thickness of 0.5 to 5 μm;
   (c) said first and second portions are continuously formed, with no boundary therebetween by quenching and freeze drying a solution of a polyamino acid under vacuum in a mold including the reinforcing material; and
   (d) the first portion has pores having diameters which decrease from the wound surface toward the second portion.

2. A wound dressing claimed in claim 1 wherein said first layer of said dressing is a sponge layer.

3. A wound dressing claimed in claim 1 wherein said reinforcing material is flexible.

4. A wound dressing according to claim 1 wherein said first layer portion has pores of 20 to 500 μm in diameter.

5. A wound dressing according to claim 1 wherein the second layer has pores and said pores are not more than 20 μm in diameter.

6. The wound dressing of claim 1 further comprising a coating on a surface of the wound dressing having a high affinity to tissues.

7. A wound dressing of a porous layer structure having good affinity to tissues of organisms comprising:
  (a) a first portion having a reinforcing material embedded therein, said first portion adapted to be placed on the wound surface, having a thickness of 1 to 10 mm and containing an antimicrobial agent in an amount of not more than 50% by weight; and
  (b) a second portion superimposed on the first portion, said second portion having a thickness of 0.5 to 5 $\mu$m, and containing an antimicrobial agent in an amount of 10 to 80% by weight;
  (c) said first and second portions are continuously formed, with no boundary therebetween by quenching and freeze drying a solution of a polyamino acid under vacuum in a mold including the reinforcing material; and
  (d) the first portion has pores having diameters which decrease from the wound surface toward the second portion.

8. A wound dressing claimed in claim 7 wherein said first layer of said dressing is a sponge layer.

9. A wound dressing claimed in claim 7 wherein said reinforcing material is flexible.

10. A wound dressing according to claim 7 wherein said first layer portion has pores of 20 to 500 $\mu$m in diameter.

11. A wound dressing according to claim 7 wherein the second layer has pores and the pores of the second portion are not more than 20 $\mu$m in diameter.

12. The wound dressing of claim 7 further comprising a coating on a surface of the wound dressing having a high affinity to tissues.

* * * * *